(12) United States Patent
Ota et al.

(10) Patent No.: US 6,479,627 B1
(45) Date of Patent: Nov. 12, 2002

(54) AQUEOUS PREPARATION OF LACTOFERRIN HAVING IMPROVED STABILITY

(75) Inventors: Atsutoshi Ota, Ikoma (JP); Mitsuaki Kuwano, Ikoma (JP); Hiroyuki Asada, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/463,773

(22) PCT Filed: Jul. 28, 1998

(86) PCT No.: PCT/JP98/03342

§ 371 (c)(1),
(2), (4) Date: Jan. 31, 2000

(87) PCT Pub. No.: WO99/06065

PCT Pub. Date: Feb. 11, 1999

(30) Foreign Application Priority Data

Jul. 31, 1997 (JP) .............................................. 9-205129

(51) Int. Cl.$^7$ .......................... C07K 14/00; C07C 57/13
(52) U.S. Cl. ...................... 530/300; 530/395; 530/400; 530/832; 514/2; 560/1; 560/125; 560/127
(58) Field of Search .......................... 424/535; 530/350, 530/400, 832, 395; 514/2; 560/1, 125, 127

(56) References Cited

U.S. PATENT DOCUMENTS

| | | | | |
|---|---|---|---|---|
| 4,978,528 A | | 12/1990 | Degre ........................ | 424/94.4 |
| 5,151,265 A | | 9/1992 | Hwang-Felgner et al. .. | 424/85.5 |
| 5,340,924 A | * | 8/1994 | Tomita et al. ............... | 530/395 |
| 5,496,718 A | | 3/1996 | Hashimoto et al. ......... | 435/232 |
| 5,543,392 A | * | 8/1996 | Tomita et al. ................ | 514/8 |
| 5,561,109 A | | 10/1996 | Mita et al. .................... | 514/12 |
| 5,929,224 A | * | 7/1999 | Suzuki et al. ............... | 536/23.5 |

FOREIGN PATENT DOCUMENTS

| | | |
|---|---|---|
| EP | 0385279 A | 9/1990 |
| EP | 0454084 A | 10/1991 |
| EP | 0513898 A | 11/1992 |
| EP | 0 576 294 | 12/1993 |
| EP | 0826373 A | 3/1998 |
| EP | 826373 * | 3/1998 |
| EP | 0926499 A | 6/1999 |
| EP | 926499 * | 6/1999 |
| JP | 2-48534 | 2/1990 |
| JP | 3-500882 | 2/1991 |
| JP | 3-215500 | 9/1991 |
| JP | 6-135851 | 5/1994 |
| JP | 6-153947 | 6/1994 |
| JP | 7-304798 | 11/1995 |
| JP | 07304798 * | 11/1995 |
| JP | 8-301785 | 11/1996 |
| JP | 9-12473 | 1/1997 |
| JP | 9-111140 | 4/1997 |
| WO | WO 92/08477 | 6/1993 |

OTHER PUBLICATIONS

Abe et al. 'Heat Stability of Boving Lactoferrin at Acidic PH', Journal fo Dairy Sciene. vol. 74, pp. 65–71, 1991.*
File Wpids on STN, An No: 1992–164314. Yotsuba Nyugyo KK, JP 04104830 A 19920407.*
File Wpids on STN, An No: 1997–028303. Norinsuisansho Chikusan Shikenjocho, JP 08289737 A Nov. 5, 1996. Abstract only.*
The Merck Index. Tenth Edition, citation No. 6062 and 9393, 1991.*
Abe et al., "Heat Stability of Bovine Lactoferrin at Acidic pH", 1991, 74, pp. 65–71, *J. Dairy Sci.*

* cited by examiner

Primary Examiner—Christopher S. F. Low
Assistant Examiner—Anish Gupta
(74) Attorney, Agent, or Firm—Frishauf, Holtz, Goodman & Chick, P.C.

(57) ABSTRACT

An object of the present invention is to provide an aqueous solution of lactoferrin which can be preserved for a long period of time. The aqueous preparation according to the present invention is an aqueous preparation which is characterized by containing a polyvalent inorganic or organic acid or a salt thereof whereby stability of lactoferrin is improved and is an aqueous preparation in which concentration of the polyvalent inorganic or organic acid or a salt thereof is 0.005% (w/v) or more. In the case of ophthalmic solutions, for example, the polyvalent inorganic or organic acid or a salt thereof is preferably 0.01–3.0% (w/v), particularly preferably 0.1–1.0% (w/v).

6 Claims, 2 Drawing Sheets

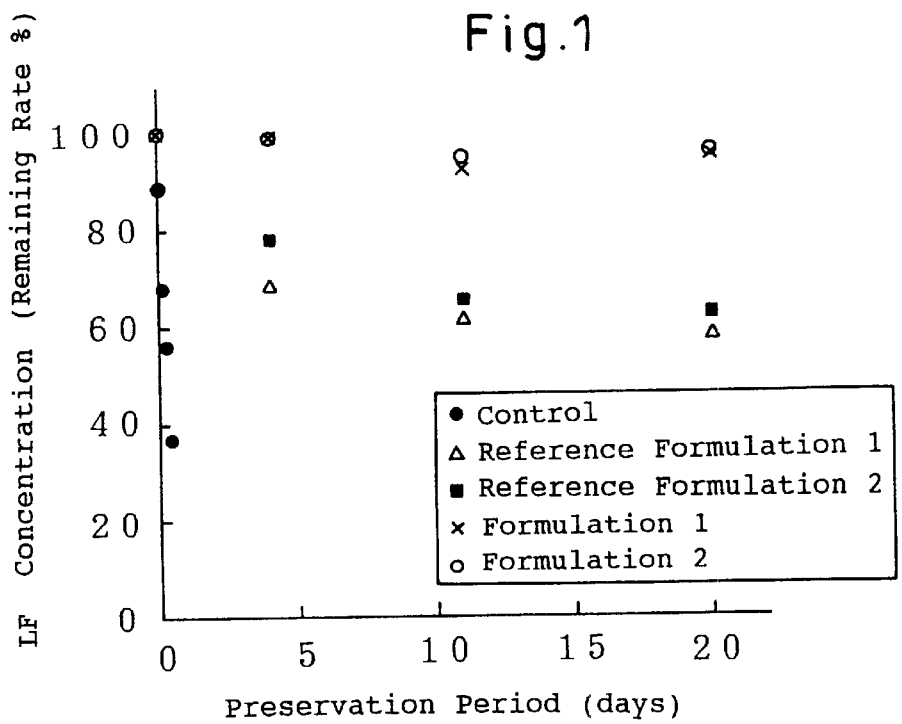
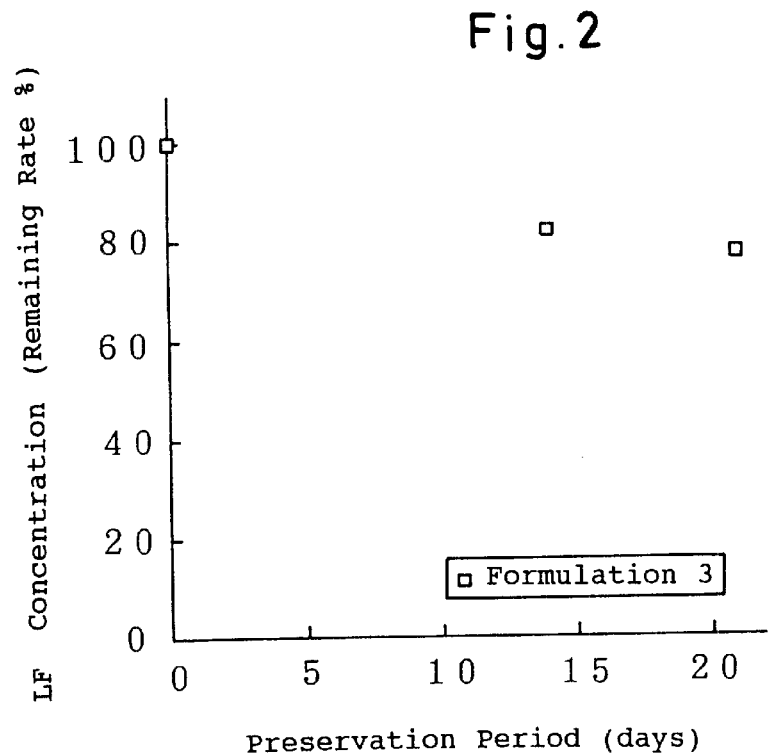

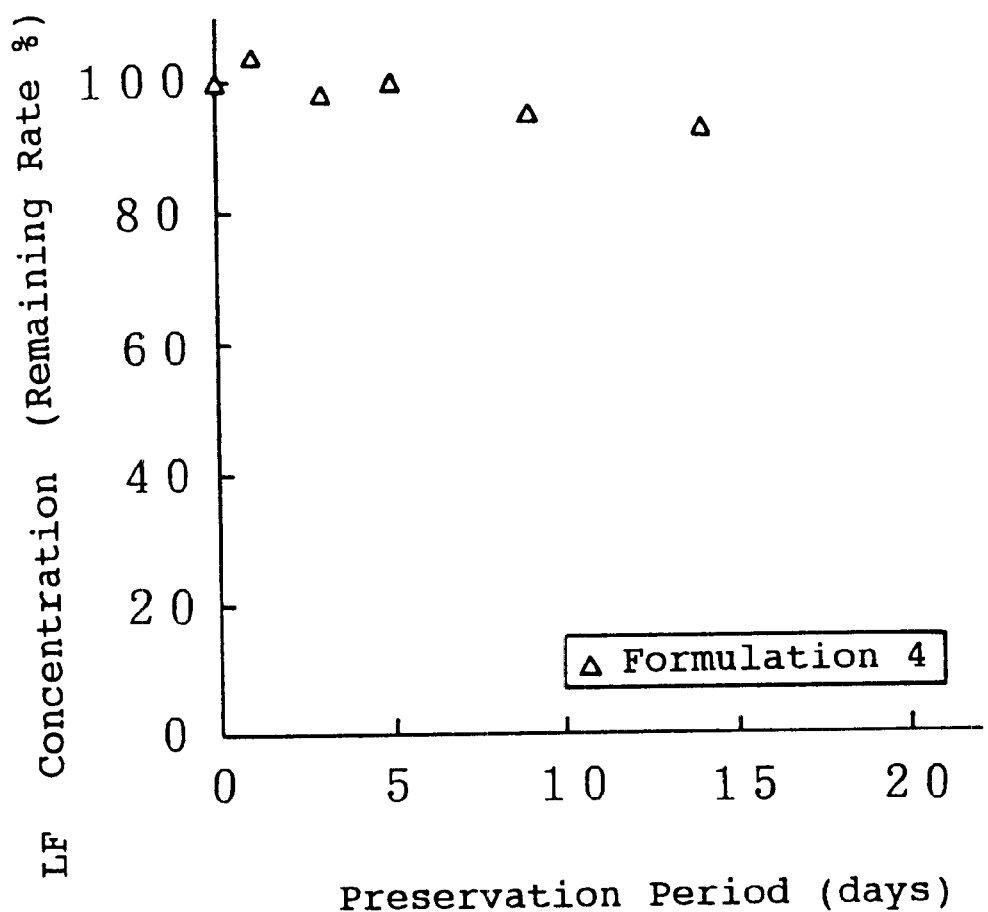

AQUEOUS PREPARATION OF LACTOFERRIN HAVING IMPROVED STABILITY

TECHNICAL FIELD

The present invention relates to an aqueous preparation of lactoferrin where stability of lactoferrin in an aqueous solution is improved and also to a method of stabilizing lactoferrin in an aqueous solution.

BACKGROUND ART

Lactoferrin is a protein existing in milk or tears of a human being, bovine, etc. and is known to have pharmacological effects such as an antibacterial effect and a lymphocyte proliferation effect (Japanese Laid-Open Patent Publication Hei-02/48534). It is also reported that lactoferrin is useful as a therapeutic agent of corneal disorders due to its excellent promotive effects of corneal keratocytes proliferation (WO 2/08477); is useful as a preventive agent of postoperative astigmatism due to its enhancing effects of wound closure strength (Japanese Laid-Open Patent Publication Hei-08/301785); and is useful as a promotive agent of mucin production due to its excellent accelerating effects of producing proteins containing mucin (Japanese Laid-Open Patent Publication Hei-09/12473).

In addition, physiologically active protein substances such as lactoferrin can be produced in large quantities due to progress in manufacturing technique and have been widely studied for their utilization as pharmaceuticals.

However, physiologically active protein substances are generally unstable as compared with ordinary low-molecular synthetic compounds and are poorly soluble in water and very difficult to be applied to aqueous preparations.

In particular, with regard to stability, they have problems such as decomposition, deamidation, dimerization and oxidation caused by chemical factors and phase transition, aggregation in a manner of noncovalent bond, adsorption caused by physical factors whereby it is difficult to maintain their stability in aqueous preparations. Lactoferrin also has a problem that, when it is preserved for a long period of time in an aqueous solution, the content of lactoferrin remarkably lowers due to decomposition, aggregation, etc. Under such circumstances, it is quite significant to stabilize lactoferrin, which is useful as a pharmaceutical, in an aqueous solution and to develop an aqueous preparation which can be preserved for a long period of time.

DISCLOSURE OF THE INVENTION

In order to develop aqueous preparations of lactoferrin which can be preserved for a long period of time, the present inventors have studied on formulating various additives and have found that formulation of a polyvalent inorganic or organic acid or a salt thereof as an additive improves stability of lactoferrin in an aqueous solution, whereupon the present invention has been achieved.

The present invention relates to an aqueous preparation of lactoferrin having improved stability which is characterized by containing a polyvalent inorganic or organic acid or a salt thereof. The present invention also relates to a method of stabilizing lactoferrin comprising adding 0.005% (w/v) or more of a polyvalent inorganic or organic acid or a salt thereof to an aqueous solution of lactoferrin.

To be more specific, the aqueous preparation according to the present invention is characterized by containing 0.005% (w/v) or more of a polyvalent inorganic or organic acid or a salt thereof.

The polyvalent inorganic acid in the present invention stands for an inorganic acid which is capable of producing divalent or higher polyvalent anions, that is, a polybasic acid. Examples of the inorganic acid are phosphoric acid and sulfuric acid while examples of the salt are alkali salts such as sodium salt and potassium salt; alkali earth metal salts such as calcium salt; and ammonium salt. Preferred examples are sodium phosphate and sodium sulfate, and particularly preferred examples are sodium phosphate, sodium monohydrogen phosphate and sodium dihydrogen phosphate. The polyvalent inorganic acid can be used either solely or in combination thereof.

The polyvalent organic acid in the present invention stands for an organic acid which is capable of producing divalent or higher polyvalent anions. Examples of the organic acid are citric acid, maleic acid, fumaric acid, tartaric acid, succinic acid, ethylenediamine tetraacetic acid and chondroitin sulfate while examples of salts thereof are alkali salts such as sodium salt and potassium salt; alkali earth metal salts such as calcium salt; and ammonium salt. Preferred examples are sodium citrate and sodium maleate, and particularly preferred examples are sodium citrate, sodium monohydrogen citrate, sodium dihydrogen citrate, sodium maleate and sodium monohydrogen maleate.

The polyvalent organic acid can also be used either solely or in combination thereof and can be used in combination with the above-mentioned polyvalent inorganic acid.

Effects of the present invention will be described in detail in the stability test which will be mentioned later. Stability of lactoferrin in an aqueous solution is significantly improved by formulating 0.005% (w/v) or more of a polyvalent inorganic or organic acid or a salt thereof. The stability of lactoferrin increases remarkably, with increasing the concentration of the acid or its salt in the solution. Accordingly, the concentration does not need defining the upper limit and the acid or a salt thereof can be formulated up to an extent which is usually allowed for ordinary aqueous preparations. The above-mentioned inorganic or organic acid or salt thereof affects the osmotic pressure of the aqueous preparation. Aqueous preparations having too high osmotic pressure are not preferable as pharmaceuticals. In the case of ophthalmic solutions, for example, the higher the osmotic pressure, the more the irritation upon instilling them into eye. Accordingly, the acceptable upper limit of the osmotic pressure ratio is usually around two. Since the concentration of the acid or its salt varies depending upon the sort of inorganic or organic acid or a salt thereof to be formulated, it is difficult to generally define the upper limit of the concentration, but in the case of sodium dihydrogen phosphate dihydrate, for example, it is around 9.0% (w/v).

Considering a stabilizing effect and an appropriate range for osmotic pressure ratio totally, the concentration of the inorganic or organic acid or a salt thereof, in the case of Ophthalmic solutions, for example, is preferably 0.01–3.0% (w/v), more preferably 0.1–1.0% (w/v).

The concentration of lactoferrin can be appropriately selected depending upon its use and, in the case of ophthalmic solutions, for example, it is 0.01–3.0% (w/v), preferably 0.1–1.0% (w/v).

The aqueous preparation of the present invention can be widely used in life science fields including pharmaceuticals, foods and cosmetics and, particularly when it is used as pharmaceuticals, examples of the dosage form are injections, ophthalmic solutions and nasal drops which can be prepared by widely-used techniques. For example, ophthalmic solutions can be prepared using various ingredients which are commonly used for opthalmic solutions including isotonicities such as sodium chloride and concentrated glycerol; buffers such as sodium acetate buffer; nonionic surfactants such as polyoxyethylene sorbitan monooleate, polyoxyl stearate 40 and polyoxyethylene hydrogenated castor oil; and preservatives such as benzalkonium chloride and paraben. The pH can be within a range which is allowed for ophthalmic preparations and is preferably within a range of 4–8.

BRIEF EXPLANATION OF THE DRAWINGS

FIG. 1 is a graph of the relation between preservation period and remaining rate of lactoferrin showing the stabilizing effect of lactoferrin at various concentrations of disodium maleate.

FIG. 2 is a graph of the relation between preservation period and remaining rate of lactoferrin showing the stabilizing effect of lactoferrin at various concentrations of sodium dihydrogen phosphate dehydrate.

FIG. 3 is a graph of the relation between preservation period and remaining rate of lactoferrin showing the stabilizing effect of lactoferrin at various concentrations of sodium dihydrogen citrate.

BEST MODES FOR CARRYING OUT THE INVENTION

Examples showing the result of the stabilizing test of the present invention are given as hereunder although those examples are to fully understand the present invention and are not to limit the scope of the present invention.

EXAMPLES OF PREPARATIONS

1) Ophthalmic Solutions (Formulation Example a)

| | |
|---|---|
| Lactoferrin | 0.3% (w/v) |
| Sodium chloride | 0.9% (w/v) |
| Disodium maleate | 0.005% (w/v) |
| Benzalkonium chloride | 0.005% (w/v) |
| Sodium hydroxide | q.s. |
| Hydrochloric acid | q.s. |
| Sterile purified water | q.s. |
| pH | 6 |

(Formulation Example b)

| | |
|---|---|
| Lactoferrin | 0.3% (w/v) |
| Sodium chloride | 0.9% (w/v) |
| Sodium dihydrogen phosphate dihydrate | 0.08% (w/v) |
| Benzalkonium chloride | 0.005% (w/v) |
| Sodium hydroxide | q.s. |
| Hydrochloric acid | q.s. |
| Sterile purified water | q.s. |
| pH | 6 |

2) Injection (Formulation Example c)

| | |
|---|---|
| Lactoferrin | 0.3% (w/v) |
| Sodium chloride | 0.58% (w/v) |
| Sodium dihydrogen phosphate dihydrate | 1.56% (w/v) |
| Sodium hydroxide | q.s. |
| Hydrochloric acid | q.s. |
| Sterile purified water | q.s. |
| pH | 6 |

By appropriately varying the amounts of the polyvalent inorganic or organic acid or a salt thereof, lactoferrin and other additives in the above formulation examples a) to c), ophthalmic solutions or injections are prepared which contain the polyvalent inorganic or organic acid or a salt thereof at concentrations 0.005%, 0.01%, 0.03%, 0.05%, 0.1%, 0.3%, 0.5%, 1.0%, 1.5%, 2.0% or 3.0% (w/v) and lactoferrin at concentrations of 0.01%, 0.03%, 0.05%, 0.1%, 0.3%, 0.5%, 1.0%, 1.5%, 2.0% or 3.0% (w/v).

[Sample Preparation]

Seven aqueous solutions (adjusted to pH 7 with sodium hydroxide or hydrochloric acid) as shown in Table 1 were served as samples for testing the stability.

TABLE 1

| Components (w/v) | Control | Reference Formulation 1 | Reference Formulation 2 | Formulation 1 | Formulation 2 | Formulation 3 | Formulation 4 |
|---|---|---|---|---|---|---|---|
| Lactoferrin | 0.3% | 0.3% | 0.3% | 0.3% | 0.3% | 0.3% | 0.3% |
| Disodium maleate | 0 | 0.0001% | 0.001% | 0.005% | 0.01% | — | — |
| Sodium dihydrogen phosphate dihydrate | — | — | — | — | — | 0.08% | — |
| Sodium dihydrogen citrate | — | — | — | — | — | — | 0.02% |
| Sterile purified water | q.s. | q.s. | q.s. | q.s. | q.s. | q.s. | q.s. |

[Experimental Method and Results]

Each of the samples was incubated at 50° C. conducting sampling with time and concentrations of lactoferrin (hereinafter, abbreviated as LF) were determined by means of an HPLC. Remaining rates of LF were calculated according to the following formula. The results are shown in FIG. 1 to FIG. 3.

$$\text{Remaining Rate of } LF\ (\%) = \frac{(LF\ \text{concentration after Preservation})}{(LF\ \text{concentration Immediately after Preparation})} \times 100$$

[Evaluation Criteria and Consideration]

As shown in FIG. 1, when disodium maleate was used as an example of the polyvalent organic acid or a salt thereof and its lactoferrin-stabilizing effect was studied at various concentrations of disodium maleate, it was found that the above-mentioned effect increases with increasing the concentration. The preparations containing disodium maleate at concentrations of lower than 0.005% (Reference Formulations 1 and 2), after preserved for 20 days, exhibit only about 60% of remaining rate of lactoferrin, and desired stable aqueous preparations were not obtained. On the contrary, the preparations according to the present invention containing disodium maleate at concentrations of 0.005% or more (Formulations 1 and 2), exhibit 95% or higher of the remaining rate of lactoferrin, even after preserved for 20 days. Thus very high stabilizing effects were observed. Further, in the cases where sodium dihydrogen phosphate dehydrate, which is a salt of polyvalent inorganic acid, was formulated (Formulation 3) and sodium dihydrogen citrate, which is a salt of polyvalent organic acid, was formulated (Formulation 4), very high stabilizing effects were observed as well (FIG. 2 and FIG. 3).

In accordance with the present invention, it is now possible to improve the stability of lactoferrin in an aqueous solution by adding thereto polyvalent inorganic or organic acid or a salt thereof at concentrations of 0.005% or more. The aqueous preparation of lactoferrin having an improved stability according to the present invention can be widely used in life science fields including pharmaceuticals, foods and cosmetics and, particularly, it is capable of providing aqueous preparations for pharmaceutical uses such as injections, ophthalmic solutions and nasal drops which are stable for a long period of time.

Industrial Applicability

The present invention relates to an aqueous preparation of lactoferrin where stability of lactoferrin in an aqueous solution is improved and also to a method of stabilizing lactoferrin in an aqueous solution.

What is claimed is:

1. A method of stabilizing lactoferrin comprising adding 0.005% (w/v) or more of a polyvalent inorganic acid or a polyvalent organic acid or a salt thereof to an aqueous solution comprising lactoferrin.

2. The method according to claim 1, wherein said inorganic acid is added and said inorganic acid is phosphoric acid or sulfuric acid.

3. The method according to claim 1, wherein said organic acid is added and said organic acid is citric acid, maleic acid, fumaric acid, tartaric acid, succinic acid, ethylenediamine tetraacetic acid or chondroitin sulfate.

4. The method according to claim 3, wherein the concentrate of lactoferrin is 0.01–3.0% (w/v).

5. The method according to claim 1, wherein the concentration of lactoferrin is 0.1–1.0% (w/v) and said aqueous solution has a pH of 4–8.

6. The method according to claim 2, wherein the concentration of lactoferrin is 0.01–3.0% (w/v).

* * * * *